US011241680B2

(12) United States Patent
Plenio et al.

(10) Patent No.: US 11,241,680 B2
(45) Date of Patent: Feb. 8, 2022

(54) RUTHENIUM-BASED METATHESIS CATALYSTS, PRECURSORS FOR THEIR PREPARATION AND THEIR USE

(71) Applicant: Umicore AG & Co. KG, Hanau-Wolfgang (DE)

(72) Inventors: Herbert Plenio, Bensheim (DE); Pavlo Kos, Griesheim (DE); Roman Savka, Griesheim (DE)

(73) Assignee: Umicore AG & Co. KG

( * ) Notice: Subject to any disclaimer, the term of this patent is extended or adjusted under 35 U.S.C. 154(b) by 140 days.

(21) Appl. No.: 16/014,615

(22) Filed: Jun. 21, 2018

(65) Prior Publication Data

US 2018/0297019 A1 Oct. 18, 2018

Related U.S. Application Data

(62) Division of application No. 14/438,433, filed as application No. PCT/EP2013/071332 on Oct. 11, 2013, now abandoned.

(30) Foreign Application Priority Data

Oct. 29, 2012 (EP) .................................. 12190416

(51) Int. Cl.
| B01J 31/32 | (2006.01) |
| B01J 31/22 | (2006.01) |
| C07F 15/00 | (2006.01) |
| C07C 217/90 | (2006.01) |
| C07C 43/29 | (2006.01) |
| C07C 5/31 | (2006.01) |
| C07C 43/275 | (2006.01) |

(52) U.S. Cl.
CPC ....... *B01J 31/2208* (2013.01); *B01J 31/2273* (2013.01); *B01J 31/2278* (2013.01); *C07C 5/31* (2013.01); *C07C 43/275* (2013.01); *C07C 43/29* (2013.01); *C07C 217/90* (2013.01); *C07F 15/0046* (2013.01); *B01J 2231/324* (2013.01); *B01J 2231/543* (2013.01); *B01J 2531/821* (2013.01); *C07C 2531/22* (2013.01)

(58) Field of Classification Search
None
See application file for complete search history.

(56) References Cited

U.S. PATENT DOCUMENTS

| 4,939,305 | A | * | 7/1990 | Stenzenberger ...... C08F 222/40 560/14 |
| 8,609,782 | B2 | | 12/2013 | Obrecht et al. |
| 2003/0220512 | A1 | * | 11/2003 | Blechert ............. C07F 15/0046 556/13 |
| 2008/0064822 | A1 | | 3/2008 | Obrecht |
| 2009/0156766 | A1 | | 6/2009 | Lemcoff et al. |

FOREIGN PATENT DOCUMENTS

| CN | 102351172 A | 2/2012 | |
| EP | 1826220 A2 | 8/2007 | |
| EP | 2289621 A1 | 3/2011 | |
| EP | 2361683 | 8/2011 | |
| WO | WO-0214376 A2 | 2/2002 | |
| WO | WO-03044060 A2 | 5/2003 | |
| WO | WO-201191980 A1 | 8/2011 | |
| WO | WO 2013064538 A1 | * 5/2013 | ........... C07D 209/14 |

OTHER PUBLICATIONS

International Search Report for PCT/EP2013/071332 dated Jan. 15, 2014.
Disendruck, C., et al., "Predicting the Cis-Trans Dichloro Configuration of Group 15-16 Chelated Ruthenium Olefin Metathesis Complexes: A DFT and Experimental Study", Inorganic Chemistry, 2009, vol. 48, pp. 10819-10825.
Jung, J-W., et al., "Total synthesis of rodgersinol: a survey of the Cu(II)-mediated coupling of *ortho*-substituted phenols", Tetrahedron, 2010, vol. 66, No. 34, pp. 6826-6831.
Peeck, L., et al., "Fast Olefin Metathesis at Low Catalyst Loading", Chemistry European Journal, 2012, vol. 18, pp. 12845-12853.
Seo, S.-Y., et al., "Concise Synthesis of Rodgersinol and Determination of the C-10 Absolute Configuration", Journal of Organic Chemistry, 2006, vol. 72, pp. 666-668.
Tzur, E., et al., "Studies on Electronic Effects in O-, N- and S-Chelated Ruthenium Olefin-Metathesis Catalysts", Chemistry European Journal, 2010, vol. 16, pp. 8726-8737.
Yin, H., et al., "Terephthalamide Derivatives as Mimetics of Helical Peptides Disruption of the Bcl-xL/Bak Interaction", Journal of the American Chemical Society, 2005, vol. 127, No. 15, pp. 5463-5468.
Zukowska, K., et al., "Thermal Switchbility of N-Chelating Hoveyda-type Catalyst Containing a Secondary Amine Ligand", Organometallics, 2012, vol. 31, pp. 462-469.

\* cited by examiner

*Primary Examiner* — Yun Qian
(74) *Attorney, Agent, or Firm* — Faegre Drinker Biddle & Reath LLP

(57) ABSTRACT

The invention is directed to ruthenium-based metathesis catalysts of the Grubbs-Hoveyda type. The new 2-aryloxy-substituted ruthenium catalysts described herein reveal rapid initiation behavior. Further, the corresponding styrene-based precursor compounds are disclosed. The catalysts are prepared in a cross-metathesis reaction starting from styrene-based precursors which can be prepared in a cost-effective manner.

The new Grubbs-Hoveyda type catalysts are suitable to catalyze ring-closing metathesis (RCM), cross metathesis (CM) and ring-opening metathesis polymerization (ROMP). Low catalyst loadings are necessary to convert a wide range of substrates including more complex and critical substrates via metathesis reactions at low to moderate temperatures in high yields within short reaction times.

5 Claims, 4 Drawing Sheets

RUTHENIUM-BASED METATHESIS CATALYSTS, PRECURSORS FOR THEIR PREPARATION AND THEIR USE

CROSS-REFERENCE TO RELATED APPLICATIONS

This application is a divisional application of U.S. patent application Ser. No. 14/438,433, filed Apr. 24, 2015, which is a national stage application (under 35 U.S.C. § 371) of PCT/EP2013/071332, filed Oct. 11, 2013, which claims benefit of European Application No. 12190416.3, filed Oct. 29, 2012, both of which are incorporated herein by reference in their entirety.

The present invention is directed to ruthenium-based metathesis catalysts, which are of the Grubbs-Hoveyda type. The new 2-aryloxy-substituted O-chelating Ru-based catalysts described herein allow rapid metathesis reactions even at mild reaction conditions such as at low temperatures and short reaction times. They reveal a rapid initiation behavior.

In a further aspect, the invention is directed to new styrene-based precursors, which are intermediate products for the preparation of the ruthenium-based catalysts of the present invention. These styrene-based precursors can be prepared in a cost- and time-effective manner and allow for an economic and straightforward preparation of the new metathesis catalysts described herein.

The invention further provides a method for producing the new ruthenium-based catalysts starting from the styrene-based precursors and also relates to the use of the new Ru-based catalysts for olefin metathesis. The method according to the present invention is characterized by few reaction steps and allows for the synthesis of the Ru-based catalysts with excellent yields. Thus the method is suitable to be adopted directly to synthesize the catalysts according to the present invention in a commercial production scale.

The Ru-based catalysts are especially suitable to catalyze ring-closing metathesis (RCM), cross metathesis (CM) and ring-opening metathesis polymerization (ROMP). The new catalysts combine fast catalyst initiation with exceptional activity in olefin metathesis reactions. Low catalyst loadings are sufficient to convert a wide range of substrates via metathesis reactions.

Ru-based catalysts for olefin metathesis reactions are known from the prior art and have gained more and more importance over the past decade. Generally, the olefin metathesis reaction comprises a metal-catalyzed rearrangement of carbon-carbon double bonds and is especially important in the production of complex natural products and polymers. However, such reactions tend to be limited by its initiation rate. Consequently, fast olefin metathesis transformation requires elevated temperatures or rapidly initiating precatalysts.

Ru-based catalysts are particularly suited for catalyzing such reactions. This is due to their high stability and wide tolerance toward various functional groups. Since their first introduction, these catalysts have been enhanced in their stability and reactivity by various alterations of the respective ligands. The Hoveyda-Grubbs type catalysts known from the prior art are typically characterized by a 2-isopropoxy-group at a benzylidene ligand (ref to formula (a)). The oxygen atom is bound to the ruthenium atom in a chelating manner.

The respective metathesis catalyst has been described in WO 02/14376 A2. A catalyst loading of about 1 mol-% to 5 mol-%, moderate to high reaction temperatures and reaction times of up to 44 hours were necessary for obtaining a sufficient yield of RCM reaction product depending on the respective substrates.

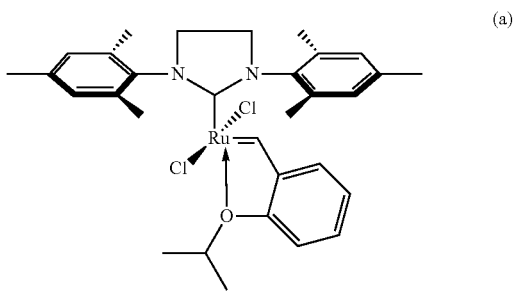

(a)

In a later development, modifications have been made on the benzylidene group by introducing electron-withdrawing and electron-donating groups (Y, Z) at the 4- and 5-position of the six-membered ring which has an impact on the Ru=CHR bond as well (see formula (b)).

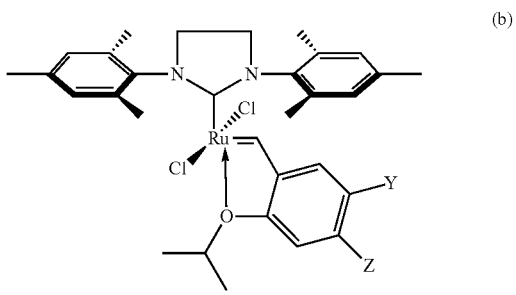

(b)

Such modified metathesis catalysts have been prepared by Lemcoff, Tzur et al. It is mentioned that the catalysts show activity for ring-closing metathesis and cross metathesis. Respective experimental data revealed sufficient yields of the respective reaction products with catalyst loadings of between 1 mol-% and 2.5 mol-%. Lower yields were obtained when using the cited catalysts in more challenging metathesis reactions such as cross metathesis (ref. to Tzur, E., Szadkowska, A., Ben-Asuly, A., Makal, A., Goldberg, I., Wozniak, K., Grela, K., Lemcoff, N. G., *Chem. Eur. J.* 2010, 16, 8726-8737).

Furthermore, various olefin metathesis catalysts have also been reported by Lemcoff et al., suggesting nitrogen, sulfur, selenium and phosphorus as chelating atoms (ref. to Diesendruck, C. E., Tzur, E., Ben-Asuly, A., Goldberg, I., Straub, B. F., Lemcoff, N. G., *Inorg. Chem.* 2009, 48, 10819-10825). Grela et al. have reported pyridine-based ruthenium catalysts bearing a chelating nitrogen atom. Ruthenium catalysts containing an amine chelating ligand have also been reported by Grela et al. (ref. to Zukowska, K., Szadkowska, A., Pazio, A. E., Wozniak, K., Grela, K., *Organometallics* 2012, 31, 462-469). High temperatures, long reaction times of several hours up to several days as well as moderate to high catalyst loading were necessary for obtaining sufficient yield of the respective metathesis reaction products.

N-chelated Grubbs-Hoveyda type catalysts have also been provided by Plenio, Peeck et al. (ref to formula (c) and (d)). However, the preparation of the N-chelated catalysts is expensive and time-consuming especially due to fact that the precursors can only be obtained by a laborious and expensive preparation method comprising several reaction steps (ref. to Peek, L. H., Savka, R. D., Plenio, H., *Chem. Eur. J.* 2012, 18, 12845-12853).

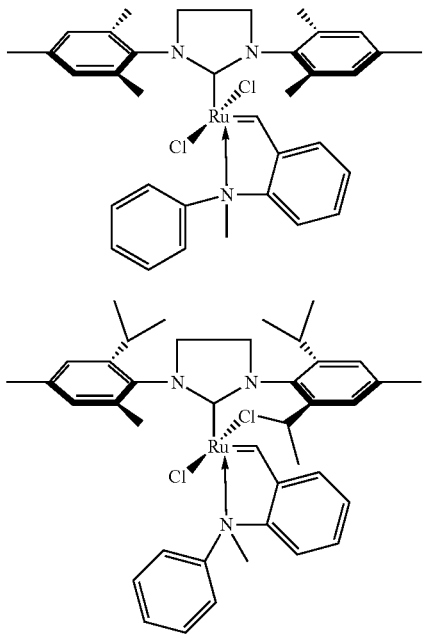

In summary, the ruthenium-based catalysts known from the prior art have the drawback of slow initiation rates requiring elevated reaction temperatures and/or demanding a moderate to high catalyst loading for obtaining a sufficient yield of a metathesis reaction product. Thus, catalysts known from the prior art usually have low to moderate activity. Further, as outlined above, the catalysts (c) and (d), recently described by Peek, Savka and Plenio require laborious and expensive preparation steps.

It is one object of the present invention to overcome the drawbacks of the metathesis catalysts known from the prior art. Thus, stable and rapidly initiating Ru-based catalysts, which are of the Grubbs-Hoveyda type and suitable for metathesis reactions, are provided in the present invention. It is a further object of the present invention to provide catalysts, which enable high substrate conversion rates in metathesis reactions even with sterically demanding substrates, such as in RCM with tri-substituted olefinic substrates.

Further, new styrene-based precursors are presented, which are suitable for the synthesis of the Ru-based catalysts of the present invention and which can usually be prepared cost-effectively with high yield in a few reaction steps starting from commercially available raw materials. Still further, the invention also provides a method which allows a cost-effective production of the new Ru-based catalysts with high yields starting from the corresponding styrene-based precursors reported herein. The new catalysts should be suitable to catalyze olefin metathesis reactions with high yields even at low catalyst loadings. The catalysts should also be capable of catalyzing olefin metathesis reactions under low to moderate temperatures within short reaction times. Thus, the catalysts should possess an increased catalytic activity compared to the activity of catalysts known from the art. The catalyst should be suitable to catalyze different types of olefin metathesis reactions of a broad range of various substrates. Finally, the Hoveyda-Grubbs type catalysts should allow for metathesis reactions under standard inert techniques such as Schlenk techniques without the need of special precautions.

The objects of the invention are solved by the subject-matter of the claims. The object is especially solved by the provision of new Ru-based catalysts of the Grubbs-Hoveyda type and by the provision of styrene-based precursors for their preparation.

The catalysts are obtainable starting from the styrene-based precursors according to the present invention by a cross metathesis reaction with Ru-based starting complexes in a single-reaction step.

The styrene-based precursors for producing the new Ru-based catalysts of the present invention are characterized by formula (I)

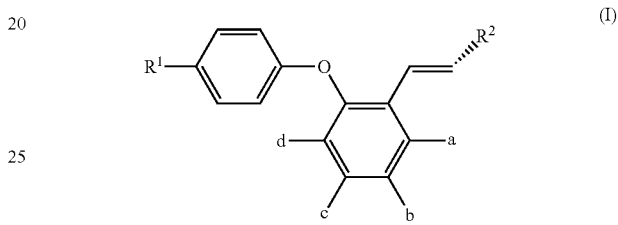

wherein
a, b, c and d are, independently from each other, selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, optionally substituted $C_6$-$C_{14}$-aryl, optionally substituted $C_6$-$C_{14}$-aryloxy, optionally substituted $C_6$-$C_{14}$-heteroaryl or electron-withdrawing groups (EWG);
$R^1$ is selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, $C_1$-$C_{10}$-dialkylamino, $C_6$-$C_{14}$-aryl, $C_6$-$C_{14}$-aryloxy, $C_6$-$C_{14}$-heterocyclic or electron-withdrawing groups (EWG), and
$R^2$ selected from hydrogen, straight chain or branched $C_1$-$C_{10}$-alkyl groups.

EWGs are atoms or functional groups that withdraw electron density from neighboring atoms. Suitable EWGs according to the present invention are selected from halogen atoms, trifluormethyl (—$CF_3$), nitro (—$NO_2$), sulfinyl (—SO—), sulfonyl (—$SO_2$—), formyl (—CHO), $C_1$-$C_{10}$-carbonyl, $C_1$-$C_{10}$-carboxyl, $C_1$-$C_{10}$-alkylamido, $C_1$-$C_{10}$-aminocarbonyl, nitrile (—CN) or $C_1$-$C_{10}$-sulfonamide groups.

$R^1$ in formula (I) is preferably selected from straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, $C_1$-$C_{10}$-dialkylamino, $C_6$-$C_{14}$-aryl, $C_6$-$C_{14}$-aryloxy, $C_6$-$C_{14}$-heterocyclic or electron-withdrawing groups (EWG). It is further preferred that $R^1$ in formula (I) is selected from $C_1$-$C_{10}$-alkylamino, $C_1$-$C_{10}$-dialkylamino, halogen atoms or nitro (—$NO_2$). Most preferably, $R^1$ in formula (I) is selected from dimethylamino (—$NMe_2$), nitro (—$NO_2$) and chlorine (—Cl).

$R^2$ is selected from hydrogen or straight chain or branched $C_1$-$C_{10}$-alkyl groups. Preferably, $R^2$ is hydrogen, methyl, ethyl, n-propyl, iso-propyl, n-butyl or iso-butyl. In a most preferred version, $R^2$ is hydrogen or methyl.

Preferably, a, b, c and d are, independently from each other, selected from hydrogen, straight chain or branched alkyl groups including $C_1$-$C_{10}$-alkyl, $C_1$-$C_{10}$-alkoxy or EWGs. In a preferred embodiment, a, b, c and d each are hydrogen.

According to a further preferred embodiment, the styrene-based precursor for the preparation of the new Ru-based catalysts is characterized by formula (Ia):

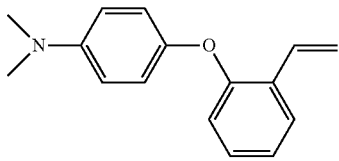

(Ia)

According to an alternative embodiment, the styrene-based precursor is characterized by formula (Ib):

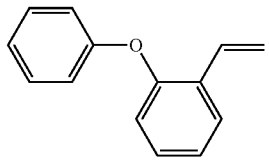

(Ib)

According to a further embodiment, the styrene-based precursor is characterized by formula (Ic):

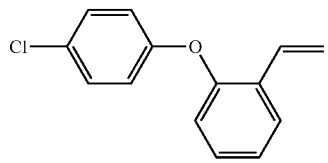

(Ic)

In a further embodiment, the styrene-based precursor is characterized by formula (Id):

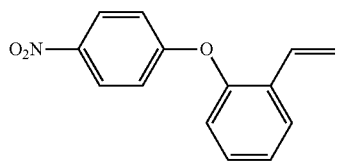

(Id)

The styrene-based precursors of the present invention may be easily obtained from the corresponding benzaldehyde intermediates via a single step reaction by nucleophilic substitution.

The conditions for the preparation of the benzaldehyde intermediates are exemplarily presented in the examples section. They can be obtained cost-effectively with a yield of more than 60%. The benzaldehyde intermediates are, for example, obtained by stirring a mixture comprising starting materials and a reaction solvent such as a chlorinated hydrocarbon solvent, at a temperature in the range of 50° C. to 200° C. depending on the respective starting materials for a period in the range of 1 to 12 hours. After stirring, the benzaldehyde intermediates are usually isolated and further purified by conventional methods.

The low-cost raw materials for producing the benzaldehyde intermediates are commercially available and may comprise a 4-substituted phenol and 2-fluorobenzaldehyde. Alternatively, the raw materials may comprise a 4-substituted 1-fluoro-benzene and a 2-hydroxy benzaldehyde.

The inventive styrene-based precursors may be easily obtained from the benzaldehyde intermediates by reaction with Wittig reagent via a single step reaction. The conditions for the reaction are exemplarily presented in the examples section.

The Ru-based catalysts of the present invention are obtainable starting from the styrene-based precursors according to the present invention by a cross metathesis reaction with a Ru-based starting complex. The Ru-based catalysts described herein are especially suitable to catalyze olefin metathesis reactions with a superior activity even at low catalyst loadings and low to moderate temperatures.

The Ru-based catalysts of the present invention are characterized in that two aryl groups are directly bonded to the chelating oxygen atom, i.e. the Ru-based catalysts are 2-aryloxy-substituted Grubbs-Hoveyda type catalysts. The aryl group of the 2-aryloxy-substituent is characterized in that it has one substituent which is in para position with respect to the attached oxygen atom. This unexpectedly allows for superior catalytic activity and fast initiation rates of the Ru-based catalysts. The Ru-based catalysts of the present invention are described by formula (II):

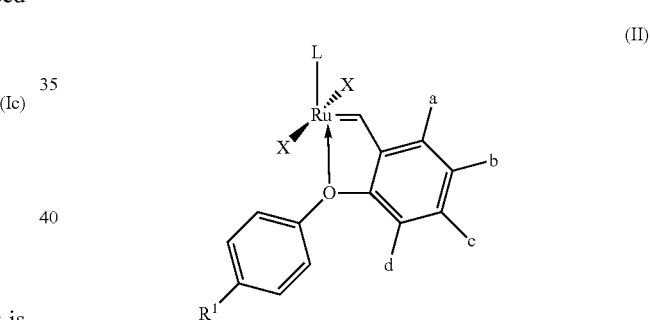

(II)

wherein

L is a neutral two-electron donor ligand;

a, b, c and d are, independently from each other, selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, optionally substituted $C_6$-$C_{14}$-aryl, optionally substituted $C_6$-$C_{14}$-aryloxy, optionally substituted $C_6$-$C_{14}$-heteroaryl or electron-withdrawing groups (EWG);

$R^1$ is selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, $C_1$-$C_{10}$-dialkylamino, $C_6$-$C_{14}$-aryl, $C_6$-$C_{14}$-aryloxy, $C_6$-$C_{14}$-heterocyclic or electron-withdrawing groups (EWG);

X is an anionic ligand independently selected from the group of halogen anions (i.e. chloride, bromide or iodide), tetrafluoroborate ($BF_4^-$) or acetate ($CH_3COO^-$).

In this formula, L represents a neutral two-electron donor ligand. Generally, the neutral two-electron donor ligand is selected from the group of phosphine ligands and the group of N-heterocyclic carbene ligands (NHC ligands). Preferably, the neutral two-electron donor ligand is selected from the group of N-hetero-cyclic carbene ligands (NHC ligands).

The phosphine ligands may be selected from the group of alkylphosphines such as tri-iso-propylphosphine, tricyclohexylphosphine (PCy$_3$) and tricyclopentylphosphine. Further, the phosphine ligand may be a phospha-bicycloalkane compound such as 9-phosphabicyclo-[3.3.1]-nonane or 9-phosphabicyclo-[4.2.1]-nonane (also named "phobanes"). Preferably, the phospha-bicycloalkane compound is selected from the group of 9-cyclohexyl-9-phospha-bicyclo-[3.3.1]-nonane ("cyclohexylphobane"), 9-(2,2,4-trimethylpentyl)-9-phospha-bicyclo-[3.3.1]-nonane (2,2,4-trimethylpentyl "phobane") and 9-isobutyl-9-phospha-bicyclo-[3.3.1]-nonane ("isobutylphobane").

In a preferred embodiment, L is an N-heterocyclic carbene ligand (NHC ligand). According to the present invention, NHC ligands are N-containing heterocycles comprising stable singlet carbenes that act as excellent two electron donor ligands towards ruthenium. The NHC ligand comprises at least one nitrogen atom and carbon atoms as ring atoms. At least one nitrogen ring atom is bound to a further moiety which is not part of the heterocyclic ring structure. The NHC ligand preferably comprises at least two nitrogen atoms as ring atoms and may be saturated or unsaturated.

The NHC ligand is preferably selected from formula (III) or (IV):

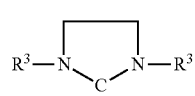

(III)

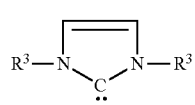

(IV)

In formula (III) and (IV), R$^3$ is a substituted aryl group selected from 2,4,6-trimethylphenyl ("mesityl"), 2,6-di-isopropylphenyl, 3,5-di-tert.-butylphenyl and 2-methylphenyl and combinations thereof.

Preferably, the NHC ligand is selected from the group of 1,3-bis-(2,4,6-trimethylphenyl)-imidazolidine-2-ylidene ("SIMes"), 1,3-bis-(2,6-di-isopropylphenyl)imidazolidine-2-ylidene ("SIPr") or 1,3-bis-(2,6-di-isopropylphenyl)-imidazoline-2-ylidene (unsaturated NHC, "IPr").

X is an anionic ligand, preferably from the group of halogen anions such as chloride, bromide or iodide; in a most preferred embodiment, X is Cl$^-$.

The groups a, b, c and d and the EWG substituents are defined as described above for the styrene-based precursor of formula (I).

R$^1$ in formula (II) is preferably selected from hydrogen, C$_1$-C$_{10}$-alkylamino, C$_1$-C$_{10}$-dialkylamino, halogen atoms or nitro (—NO$_2$). Most preferably, R$^1$ in formula (II) is selected from hydrogen, dimethylamino (—NMe$_2$), nitro (—NO$_2$) and chlorine (—Cl).

Preferably, a, b, c and d are, independently from each other, selected from hydrogen, straight chain or branched alkyl groups including C$_1$-C$_{10}$-alkyl, C$_1$-C$_{10}$-alkoxy or electron-withdrawing groups (EWG). In a further preferred embodiment, a, b, c and d each are hydrogen. In case a, b, c and d are each hydrogen, Ru-based catalysts having superior catalytic activity are obtained. In such catalysts, the Ru—O bond is primarily influenced.

In a specific embodiment, the Ru-based catalyst according to the present invention is characterized by formula (IIa):

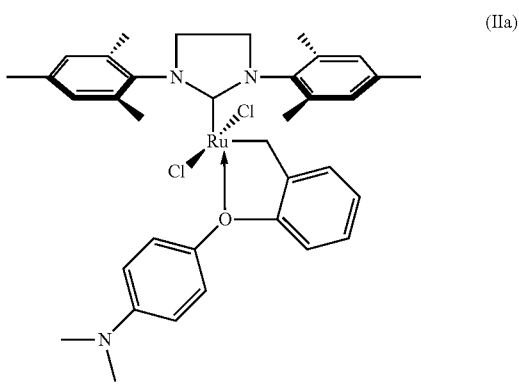

(IIa)

In a further specific embodiment, the Ru-based catalyst of the present invention is characterized by formula (IIb):

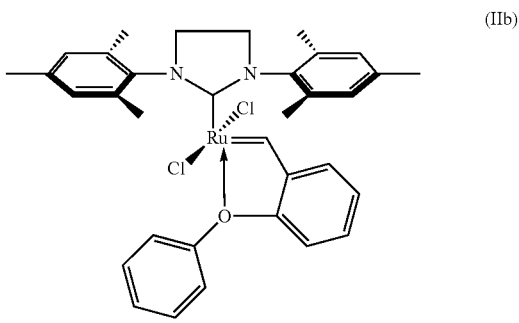

(IIb)

In further specific embodiments, the inventive Ru-based catalyst is characterized by formula (IIc) or formula (IId):

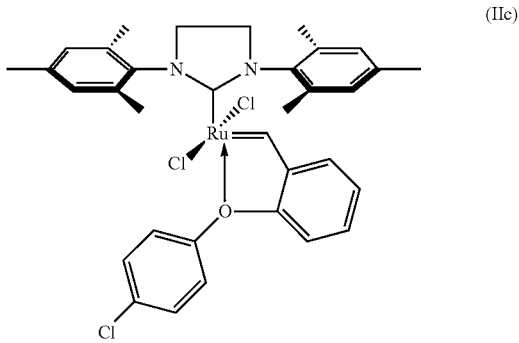

(IIc)

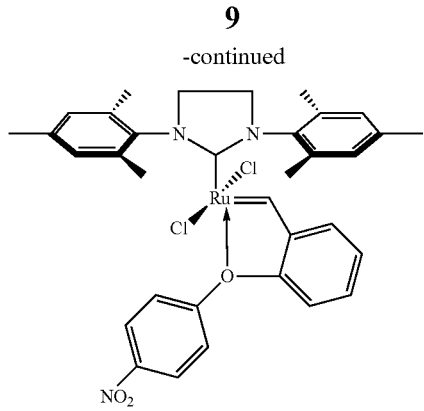

(IId)

In further alternative embodiments, the provided Ru-based catalyst is characterized by one of formulas (IIe), (IIf), (IIg) or (IIh), preferably by formula (IIe) or by formula (IIf):

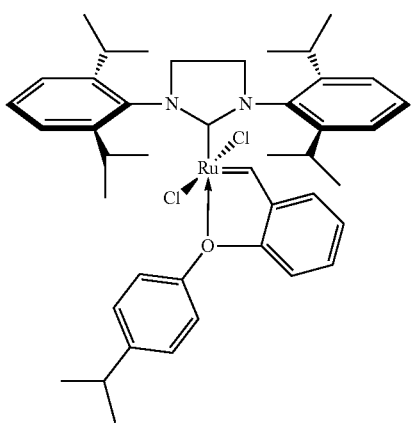

(IIe)

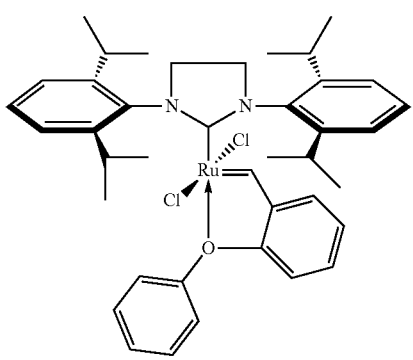

(IIf)

(IIg)

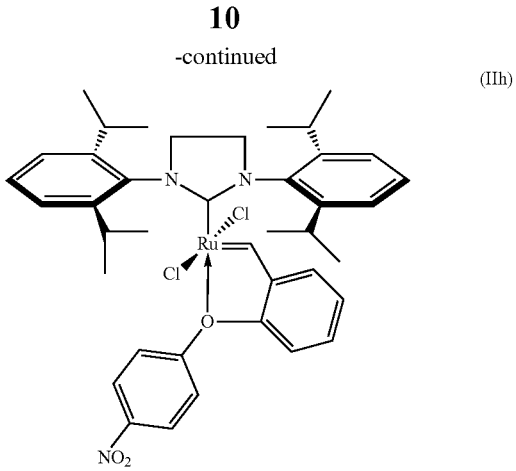

(IIh)

In addition to the Ru-based catalysts described above, the present invention also refers to a method for manufacturing these new Ru-based catalysts. Generally, the present catalysts are obtainable from the new styrene-based precursors of formula (I) via a single-step reaction. A single step reaction according to the present invention is a reaction that precedes without necessitating intermediate isolation or intermediate purification steps (hereinafter called "one-pot synthesis").

A variety of Ru-based starting complexes of the general formula $L_2X_2Ru=CR_xR_y$ (wherein $R_x$ and $R_y$ may be independently hydrogen, alkyl or aryl and wherein $R_x$ and $R_y$ may form a ring) can be employed as starting material for the preparation of the catalysts of the present invention. Examples of suitable Ru-based starting complexes are the well-known Ru-benzylidene complexes of Grubbs 1$^{st}$ generation (containing phosphine ligands) or the Grubbs 2$^{nd}$ generation Ru-complexes (containing NHC ligands).

In a preferred method of the invention, the styrene-based precursor of formula (I) is reacted with a Ru-based starting complex of formula (V) in a cross metathesis reaction to yield the Ru-based catalysts of formula (II). This reaction is shown in Scheme 1.

Scheme 1

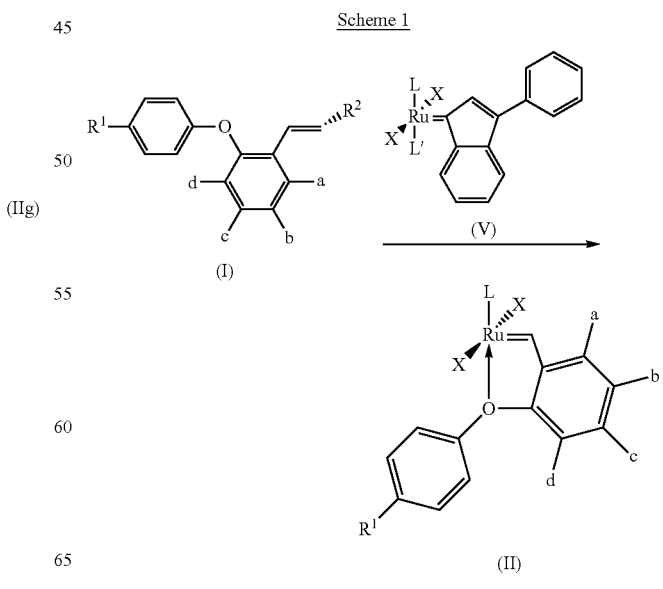

In the Ru-based starting complex of formula (V), L may be a phosphine ligand selected from the group of triisopropylphosphine, tricyclohexylphosphine (PCy$_3$), tricyclopentylphosphine and phospha-bicycloalkane compounds such as 9-cyclohexyl-9-phospha-bicyclo-[3.3.1]-nonane ("cyclohexylphobane"), 9-(2,2,4-trimethylpentyl)-9-phospha-bicyclo-[3.3.1]-nonane (2,2,4-trimethylpentyl phobane") and 9-isobutyl-9-phospha-bicyclo-[3.3.1]-nonane ("isobutylphobane").

In a preferred version of the method, L is a NHC ligand selected from the group of 1,3-bis-(2,4,6-trimethylphenyl)-imidazolidine-2-ylidene ("SIMes"), 1,3-bis-(2,6-diisopropylphenyl)-imidazolidine-2-ylidene ("SIPr") or 1,3-bis-(2, 6-di-isopropylphenyl)imidazoline-2-ylidene (unsaturated NHC, "IPr").

Further, in the Ru-based starting complex of formula (V) above, L' is a leaving ligand representing a phosphine ligand selected from the group of triisopropylphosphine, tricyclohexylphosphine (PCy$_3$), tricyclopentylphosphine, 9-cyclohexyl-9-phospha-bicyclo-[3.3.1]-nonane ("cyclohexylphobane"), 9-(2,2,4-trimethylpentyl)-9-phospha-bicyclo-[3.3.1]-nonane (2,2,4-trimethylpentyl phobane"), 9-isobutyl-9-phospha-bicyclo-[3.3.1]-nonane ("isobutylphobane") or a pyridine ligand, which may be substituted or unsubstituted. Examples are pyridine or bromopyridine. In a most preferred embodiment, L' is pyridine.

X is an anionic ligand, preferably from the group of halogen anions such as chloride, bromide or iodide; in a most preferred embodiment, X is chloride (Cl$^-$).

Preferably, the method of preparing the Ru-based catalysts according to the present invention comprises the following reaction steps:
a) providing a reaction mixture, which comprises the styrene-based precursor of formula (I), the Ru-based starting complex of formula (V) and a reaction solvent;
b) optionally stirring the mixture;
c) evaporating the reaction solvent;
d) optionally purifying the remaining reaction product.

Preferably, the molar ratio of the styrene-based precursor of formula (I) to the Ru-based starting complex of formula (V) is at least 1.00 and more preferably at least 1.01, further preferred at least 1.05. In case this molar ratio is too low, the inventive catalysts cannot be obtained with a high yield. The molar ratio of the styrene-based precursor of formula (I) to the Ru-based starting complex of formula (V) should not exceed a value of 1.5; preferably the molar ratio should not exceed a value of 1.2.

It is particularly preferred that the molar ratio of the styrene-based precursor of formula (I) to the Ru-based starting complex of formula (V) is between 1.05 and 1.15.

Depending on the Ru-based starting complex of formula (V) used, the reaction conditions for the cross metathesis reaction may be modified; in particular, the reaction mixture of reaction step a) may further comprise Cu-salts (such as CuCl or CuBr) as phosphine scavengers when using phosphine containing Ru-starting complexes such as, for example, (PCy$_3$)$_2$Cl$_2$Ru-phenylindenylidene. It should be noted, however, that the addition of Cu-salts is not necessary, if the leaving ligand L' is not a phosphine.

It is preferred that the reaction mixture of reaction step a) further comprises an acidic ion exchange resin, preferably in case the leaving ligand L' is a pyridine or tricyclohexylphosphine ligand. The preferred presence of the resin surprisingly allows for improved yields of the inventive catalysts. It is assumed that this facilitates the substitution of the leaving ligand L' by the inventive styrene-based precursor. Preferably, the resin is based on functionalized styrene divinylbenzene copolymers. The functional group is preferably of the sulphuric acid type. More preferably, the resin comprises Amberlyst® resin; most preferably, the resin is Amberlyst® resin. Suitable ion exchange resins are disclosed in WO 2011/091980 A1.

The reaction mixture comprises a reaction solvent, preferably a chlorinated hydrocarbon solvent such as dichloromethane (DCM), chloroform or 1,2-dichloroethane (DCE) or in cyclic ethers such as tetrahydrofuran (THF) or dioxane. Alternatively, aromatic hydrocarbon solvents such as benzene or toluene as well as esters and mixtures of the listed solvents may be employed. Most preferably, the reaction solvent is selected from DCM and THF.

The suitable reaction time for step b) depends on the type of the starting materials. Typically, the mixture is stirred in the range of from 0.25 to 2 hours, preferably 0.25 to 1.5 hours and most preferably 0.5 to 1 hour to complete the reaction. Reaction temperatures may vary depending on the raw materials during stirring. Typically, reaction temperatures in the range of up to 100° C., preferably up to 80° C. are appropriate. More preferably, the reaction temperatures do not exceed 50° C., especially preferably they do not exceed 45° C. The reaction is preferably carried out under an inert gas such as nitrogen or argon, most preferably argon.

Optionally, the resin is separated by filtration following reaction step b). Subsequent to reaction step b) or optionally after subsequent filtration of the acidic ion exchange resin, the reaction solvent is removed, preferably in vacuo. The remaining reaction product may be further purified. This is preferably done by washing the reaction product with a suitable solvent. Suitable solvents include aliphatic alcohols, alkanes, alkenes and mixtures thereof. Preferably, the solvent is selected from methanol, n-pentane or mixtures thereof. Further purification steps may be conducted.

The Ru-based catalysts according to the present invention are obtainable from the precursors of formula (I) by the described method within short reaction times under mild to moderate reaction conditions. This ensures a cost-effective and time-saving preparation route resulting in improved metathesis catalysts with high purity in high yield. Preferably, the Ru-based catalysts are obtainable by the described method in yields of at least 60%, more preferably at least 65% and most preferably at least 70%.

The Ru-based catalysts according to the present invention may be used to catalyze metathesis reactions with a wide range of substrates. As already described, these catalysts are particularly suitable to catalyze ring-closing metathesis (RCM), cross metathesis (CM), ring-opening metathesis polymerization (ROMP) and other metathesis reactions. In general, metathesis reactions are performed in homogenous phase. Alternatively, the reaction may be carried out in a heterogeneous manner with immobilized or supported catalysts; for example in the presence of cation-exchange resins. The reaction conditions for the metathesis reactions are well known to a person skilled in the art. The reaction is carried out in a suitable reaction solvent, which may be, for example, 1, 2-dichloroethane, hexafluorobenzene or toluene. Preferably the reaction solvent comprises toluene. Most preferably the reaction solvent is toluene. Preferably, the metathesis reaction is conducted under a protective inert gas such as nitrogen or argon, preferably argon.

The Ru-based catalysts of the present invention allow for reaction temperatures during metathesis reaction below 60° C., preferably below 55° C. Such low temperatures are important when employing temperature-sensitive substrate materials. Moreover, the catalysts according to the present invention also allow for excellent yields of reaction products even at temperatures about 0° C. This is evident from FIG. 1 and FIG. 2.

Further, the Ru-catalysts of the present invention enable exceptional low catalyst loadings. Preferably, the catalyst loading is below 1.000 ppm, i.e. below 0.1 mol-%. Further preferably, catalyst loadings of not more than 250 ppm, more preferably of not more than 100 ppm are sufficient for obtaining high conversions. Thus, the metathesis reactions can be conducted in a cost-effective manner.

The Ru-catalysts of the present invention allow for metathesis reactions with short reaction times. Typically, as shown in the experimental section, more than 60% of the substrate is converted after 15 minutes. This is measured by known methods, preferably by gas chromatography (GC). In most cases a conversion of ≥70% and preferably of ≥75% is obtained with the Ru-based catalysts of the present invention after a reaction time of at least 15 minutes under the conditions mentioned above. In various metathesis reactions, the conversion reaches 90% or even 99% after 15 minutes reaction time. In some cases, a yield of isolated finished product of >80%, more preferably ≥90% can be obtained.

The Ru-based catalysts of the present invention show a fast initiation rate and thus translate into fast and efficient olefin metathesis reactions while having an excellent catalytic activity even at low to moderate reaction temperatures. A TON ("Turn-over number"; i.e. molar ratio of converted substrate to catalyst) of preferably >3×10$^3$, further preferred ≥5×10$^3$ and still further preferred ≥8×10$^3$ and especially preferred of ≥3×10$^4$ may be obtained with the inventive new Ru-based catalysts. The TOF (TON per hour; turn-over frequency) which is a measure for the catalytic activity preferably amounts up to >1×10$^4$ h$^{-1}$, further preferred ≥2×10$^4$ h$^{-1}$ and most preferred ≥7×10$^4$ h$^{-1}$. In specific embodiments, a TOF of ≥1×10$^5$ h$^{-1}$ is obtained.

It was found by the present inventors, that it is necessary to provide the right balance between the steric and electronic effects of the substituents bonded to the chelating oxygen atom in order to tailor the activity of the catalysts of the present invention. Thus it is supposed that the excellent activity of the Ru-based catalysts compared to the ruthenium-based catalysts of formula (a) may result from a modification in the nature of the O-donor, i.e. from decreased donor properties of the oxygen atom as well as from lower steric interferences. This modification in the nature of the O-donor atom in the benzylidene ligand may contribute to a weakening of the Ru—O interaction, a higher Ru—O-distance and consequently lead to a significant increase in the initiation rate of the catalyst. It is assumed that this contributes to the fast and efficient metathesis reactions by using the new Ru-based catalysts. Up to date, such 2-phenoxy substituted Ru-catalysts have not been described in the literature.

In summary, the new Ru-based catalysts of the present invention combine fast catalyst initiation and high stability with exceptional activity in olefin metathesis reactions. Low catalyst loadings are sufficient for obtaining excellent yields of metathesis reaction products even within short reaction times and at low to moderate reaction temperatures. The new catalysts are easily obtainable with high purity and high yield in a one-step reaction from new styrene-based precursors. The styrene-based precursors are generally obtained with high yield from commercial raw materials in a cost-effective manner. Thus the new Ru-based catalysts can be manufactured economically in industrial scale.

Figure 1:
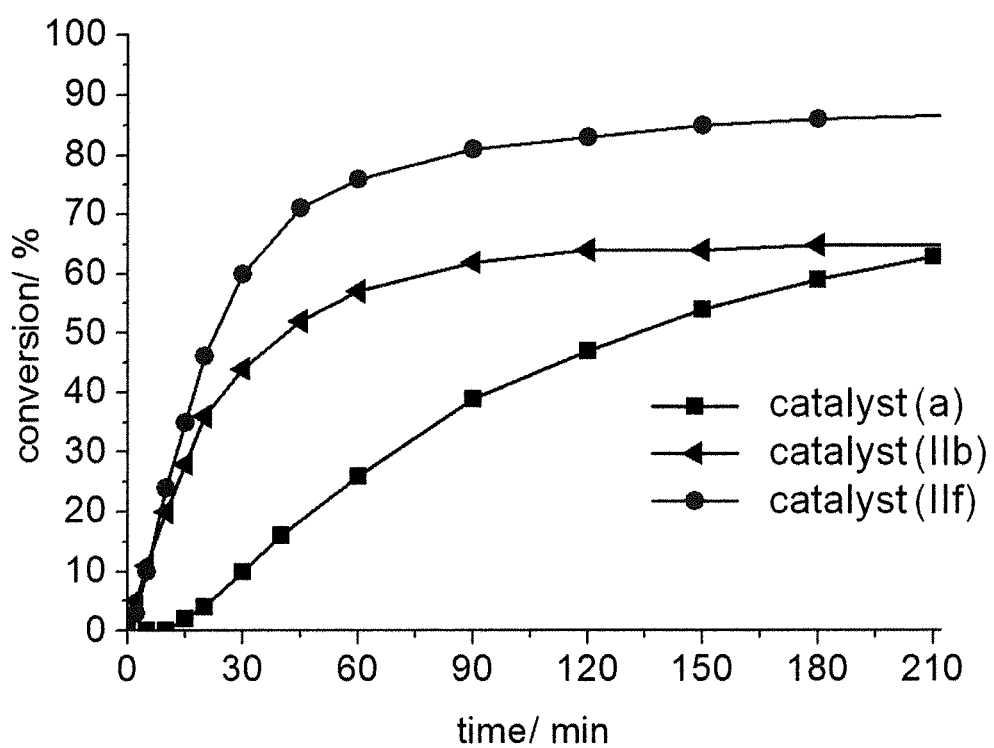
FIG. 1 shows the conversion (in %) of N,N-diallyltosylamide (0.1 mol/L) during RCM reaction over a reaction period of 210 minutes at 0° C. in toluene using 0.025 mol-% (250 ppm) of catalysts of formulas (a), (IIb) and (IIf).

The invention is further described by the following examples without limiting or narrowing the scope of protection.

EXAMPLES

General Remarks

All chemicals are purchased as reagent grade from commercial suppliers and used without further purification, unless otherwise noted. All reactions involving ruthenium complexes are performed under an atmosphere of argon. CH$_2$Cl$_2$ (99.5%) and pentane (99%) are obtained from Gruessing GmbH, toluene from Sigma-Aldrich (Lab. Reagent grade, 99.3%). These solvents are dried and degassed by using a column purification system. In this system, the solvents are sparged and pressurized with argon (0.1 to 1 bar), followed by successive passing through a column filled with activated alumina and a second column, either filled with a supported copper catalyst (pentane) or again activated alumina (CH$_2$Cl$_2$). Dimethylformamide is refluxed over calcium hydride and distilled under argon atmosphere. Tetrahydrofuran is dried over sodium and distilled under argon atmosphere. All solvents are stored over molecular sieves (4 Å).

$^1$H and $^{13}$C nuclear magnetic resonance spectra are recorded with a Bruker DRX300 spectrometer. The chemical shifts are given in parts per million (ppm) on the delta scale (δ) and are referenced to tetramethylsilane ($^1$H-, $^{13}$C-

NMR=0.0 ppm) or the residual peak of CHCl3 ($^1$H-NMR=7.26 ppm, $^{13}$C-NMR=77.16 ppm). Abbreviations for NMR data: s=singlet; d=doublet; t=triplet; q=quartet; sep=septet; m=multiplet; bs=broad signal. Preparative chromatography is performed using Merck silica 60 (0.063-0.02 mesh). GC experiments are run on a Clarus 500 GC with autosampler and FID detector. Column: Varian CP-SiI 8 CB (I=15 m, $d_i$=0.25 mm, $d_F$=1.0 Im), $N_2$ (flow: 17 cm s$^{-1}$; split 1:50); Injector-temperature: 270° C., detector temperature: 350° C.

Example 1

Preparation of the Styrene-Based Precursors (Ia) to (Id)

The preparation is carried out starting from 4-substituted phenols (for preparing styrene-based precursors of formula (Ia) to (Ic)) or starting from 4-substituted 1-fluoro-benzene for preparing styrene-based precursor of formula (Id). In the first reaction step, the respective benzaldehyde intermediates are prepared. The benzaldehyde intermediates are then converted to the respective precursor (Ia) to (Id) in a second reaction step.

a) Preparation of 2-(4-(dimethylamino)phenoxy)benzaldehyde, 2-phenoxybenzaldehyde and 2-(4-chlorophenoxy)benzaldehyde The benzaldehyde intermediates are synthesized following literature procedures with modifications. Into a dry Schlenk flask under argon atmosphere the corresponding phenol (17.7 mmol), 2-fluorobenzaldehyde (2.0 g, 16.1 mmol), potassium carbonate (5.6 g, 40.3 mmol) and anhydrous DMF (40 mL) are added at room temperature. The mixture is warmed in a sealed flask to 170° C. and stirred at this temperature for 2 h (for preparing 2-phenoxy-benzaldehyde and 2-(4-chlorophenoxy)benzaldehyde) or at 150° C. for 1.5 h (for preparing 2-(4-(dimethylamino)phenoxy)benzaldehyde). Then the mixture is allowed to cool to room temperature and is treated with water (200 mL) and the product is extracted with diethyl ether (3×50 mL). The combined organic layers are washed with NaOH (1M, 50 mL), brine (150 mL), dried over anhydrous $MgSO_4$ and evaporated in vacuum. The residue is purified by column chromatography (cyclohexane/ethyl acetate 10:1, v/v (for preparing 2-phenoxy-benzaldehyde and 2-(4-chlorophenoxy)benzaldehyde) or used in next reaction without purification (in case of 2-(4-(dimethylamino)phenoxy)-benzaldehyde).

2-(4-(dimethylamino)phenoxy)benzaldehyde is obtained as a white solid (3.07 g, 79% yield). $^1$H NMR (300 MHz, CDCl$_3$) δ 10.59 (d, J=0.8 Hz, 1H), 7.90 (dd, J=7.8, 1.8 Hz, 1H), 7.44 (ddd, J=8.5, 7.3, 1.8 Hz, 1H), 7.12-7.05 (m, 1H), 7.03-6.97 (m, 2H), 6.84-6.74 (m, 3H), 2.96 (s, 6H). $^{13}$C NMR (75 MHz, CDCl$_3$) b 189.85, 161.75, 148.14, 145.47, 135.76, 128.33, 126.05, 122.23, 121.25, 116.90, 114.18, 41.34.

2-phenoxybenzaldehyde is obtained as a yellow oil (2.52 g, 79% yield). $^1$H NMR (300 MHz, CDCl$_3$) b 10.52 (d, J=0.8 Hz, 1H), 7.94 (dd, J=7.8, 1.8 Hz, 1H), 7.51 (ddd, J=8.4, 7.3, 1.8 Hz, 1H), 7.43-7.35 (m, 2H), 7.22-7.15 (m, 2H), 7.10-7.04 (m, 2H), 6.90 (dd, J=8.4, 0.8 Hz, 1H). $^{13}$C NMR (75 MHz, CDCl$_3$) b 189.45, 160.10, 156.53, 135.85, 130.22, 128.55, 127.03, 124.44, 123.44, 119.51, 118.60.

2-(4-chlorophenoxy)benzaldehyde is obtained as a yellow solid (3.07 g, 82% yield). $^1$H NMR (500 MHz, CDCl$_3$) δ 10.48 (d, J=0.7 Hz, 1H), 7.94 (dd, J=7.8, 1.8 Hz, 1H), 7.53 (ddd, J=8.4, 7.3, 1.8 Hz, 1H), 7.37-7.33 (m, 2H), 7.24-7.19 (m, 1H), 7.03-6.99 (m, 2H), 6.89 (dd, J=8.4, 0.7 Hz, 1H). $^{13}$C NMR (126 MHz, CDCl$_3$) b 189.14, 159.62, 155.20, 135.95, 130.26, 129.65, 128.85, 127.13, 123.91, 120.72, 118.60.

b) Synthesis of 2-(4-nitrophenoxy)benzaldehyde

Into a dry Schlenk flask under argon atmosphere are added 1-fluoro-4-nitrobenzene (2.0 g, 14.2 mmol), salicylic aldehyde (2.1 g, 17.0 mmol), potassium carbonate (4.9 g, 35.5 mmol) and anhydrous DMF (40 mL). The mixture is warmed in a sealed flask to 100° C. and stirred at this temperature overnight. Then the mixture is allowed to cool to room temperature, treated with water (200 mL) and the product is extracted with diethyl ether (3×50 mL). Combined organic layers are washed with NaOH (1M in water, 50 mL) and brine (150 mL), dried over anhydrous $MgSO_4$ and evaporated in vacuo. Residue is purified by column chromatography (cyclohexane/ethyl acetate 4:1, v/v).

2-(4-nitrophenoxy)benzaldehyde is obtained as a yellow solid (2.40 g, 69% yield). $^1$H NMR (300 MHz, CDCl$_3$) δ 10.34 (d, J=0.7 Hz, 1H), 8.28-8.23 (m, 2H), 8.00 (dd, J=7.8, 1.8 Hz, 1H), 7.66 (dd, J=8.3, 7.4, 1.8 Hz, 1H), 7.41-7.35 (m, 1H), 7.13-7.06 (m, 3H).
$^{13}$C NMR (75 MHz, CDCl$_3$) δ 188.36, 162.64, 157.14, 143.61, 136.26, 129.71, 128.14, 126.31, 125.85, 120.93, 117.87. HRMS: m/z calcd for $C_{13}H_9NO_4$ 243.0542; found: 243.0531. Analysis calcd. for $C_{13}H_9NO_4$ (243.05): C 64.18, H 3.73, N 5.76; found: C 64.23, H 3.72, N 5.88.

c) Vinylation of the benzaldehyde intermediates

A Schlenk flask containing methyltriphenylphosphonium iodide (3.0 g, 7.42 mmol) is evacuated and back-filled with argon three times. Anhydrous tetrahydrofuran (50 mL) is added by syringe and the formed suspension is cooled to −10° C. KOtBu (902 mg, 8.04 mmol) is added in portions to the stirred mixture under a stream of argon, and stirring continued at −10° C. for 20 minutes. Subsequently, one of the benzaldehyde intermediates (6.18 mmol) is added. The mixture is allowed to warm to room temperature, stirred overnight and poured into water (500 mL). The product is extracted with diethyl ether (3×100 mL). The organic phases are combined, washed with brine and dried over magnesium sulfate. The solvent is removed in vacuo and the residue is purified by column chromatography (cyclohexane/ethyl acetate 20:1, v/v).

Precursor (Ia) is obtained as a colorless solid (1.18 g, 80% yield). $^1$H NMR (300 MHz, CDCl$_3$) δ 7.58 (dd, J=7.7, 1.8 Hz, 1H), 7.20-7.01 (m, 3H), 6.96-6.89 (m, 2H), 6.80 (dd, J=8.2, 1.2 Hz, 1H), 6.76 (d, J=9.0 Hz, 2H), 5.82 (dd, J=17.7, 1.4 Hz, 1H), 5.30 (dd, J=11.1, 1.4 Hz, 1H), 2.93 (s, 6H). $^{13}$C NMR (75 MHz, CDCl$_3$) δ 155.69, 147.37, 131.49, 128.89, 128.66, 126.61, 122.78, 120.11, 117.92, 115.02, 114.34, 41.51. HRMS: m/z calcd for $C_{16}H_{17}NO$ 239.1304; found: 239.1310. Analysis calcd. for $C_{16}H_{17}NO$ (239.13): C 80.30, H 7.16, N 5.85; found C 79.88, H 7.11, N 5.83.

Precursor (Ib) is obtained as a colorless solid (0.99 g, 82% yield). $^1$H NMR (500 MHz, CDCl$_3$) δ 7.62 (dd, J=7.8, 1.7 Hz, 1H), 7.34-7.30 (m, 2H), 7.24 (dd, 1H), 7.16-7.13 (m, 1H), 7.07 (tt, J=7.6, 1.1 Hz, 1H), 7.01 (dd, J=17.7, 11.1 Hz, 1H), 6.97-6.94 (m, 2H), 6.92 (dd, J=8.1, 1.1 Hz, 1H), 5.81 (dd, J=17.7, 1.3 Hz, 1H), 5.29 (dd, J=11.1, 1.3 Hz, 1H).
$^{13}$C NMR (75 MHz, CDCl$_3$) δ 158.05, 153.75, 131.12, 129.97, 129.83, 129.14, 126.77, 124.21, 122.81, 120.23, 117.91, 115.51. Elemental analysis calcd. for $C_{14}H_{12}O$ (196.09) C 85.68, H 6.16; found C 85.49, H 6.11.

Precursor (Ic) is obtained as a colorless liquid (1.20 g, 84% yield). $^1$H NMR (300 MHz, CDCl$_3$) δ 7.60 (dd, J=7.7, 1.8 Hz, 1H), 7.28-7.20 (m, 3H), 7.18-7.12 (m, 1H), 6.99-6.87 (m, 2H), 6.87-6.82 (m, 2H), 5.78 (dd, J=17.7, 1.3 Hz, 1H), 5.27 (dd, J=11.1, 1.2 Hz, 1H). $^{13}$C NMR (75 MHz, CDCl$_3$) δ 156.76, 153.32, 130.85, 130.07, 129.79, 129.26, 127.77, 126.93, 124.66, 120.33, 118.97, 115.86. HRMS: m/z calcd for C$_{14}$H$_{11}$ClO 230.0494; found 230.04815. Elemental analysis calcd. for C$_{14}$H$_{11}$ClO (230.69): C 72.89, H 4.81; found C 72.82, H 4.92.

Precursor (Id) is obtained as a yellow solid (1.15 g, 77% yield). $^1$H NMR (300 MHz, CDCl$_3$) δ 8.22-8.16 (m, 2H), 7.68-7.64 (m, 2H), 7.38-7.24 (m, 1H), 7.04-7.00 (m, 1H), 6.97-6.91 (m, 2H), 6.79 (dd, J=17.7, 11.1 Hz, 1H), 5.79 (dd, J=17.7, 1.1 Hz, 1H), 5.29 (dd, J=11.1, 1.1 Hz, 1H). $^{13}$C NMR (75 MHz, CDCl$_3$) δ 163.61, 151.47, 142.67, 130.74, 130.20, 129.65, 127.31, 126.21, 126.14, 121.73, 116.81, 116.51. HRMS: m/z calcd for C$_{14}$H$_{11}$NO$_3$ 241.0739; found: 241.0714 Elemental analysis calcd. for C$_{14}$H$_{11}$NO$_3$ (241.25) C 69.70, H 4.60, N 5.81; found C 69.93, H 4.68, N 5.69.

Example 2 a) Preparation of catalysts (IIa) to (IIc) and (IIe) to (IIh)

A flame-dried Schlenk tube containing [RuCl$_2$(SIMes)(3-phenylindeneylidene)(py)](200 mg, 0.27 mmol; Umicore AG & Co. KG, Hanau, Germany) (for preparing catalysts (IIa) to (IIc) or [RuCl$_2$(SIPr)(3-phenylindeneylidene)(py)] (200 mg, 0.24 mmol; Umicore AG & Co. KG, Hanau, Germany) (for preparing catalysts (IIe) to (IIh)) is evacuated and back-filled with argon three times. Methylene chloride (4 mL), the respective styrene-based precursor (0.30 mmol for preparing catalysts (IIa) to (IIc) or 0.26 mmol for preparing catalysts (IIe) to (IIh)) and Amberlyst resin (275 mg for preparing catalysts (IIa) to (IIc) or 250 mg for preparing catalysts (IIe) to (IIh), dry form, 4.70 mmol H$^+$/g) are added under an atmosphere of argon. The mixture is stirred at 40° C. for 30 minutes for preparing catalysts (IIa) to (IIc) or 60 minutes for preparing catalysts (IIf) to (IIh) or at room temperature for 1 h for preparing catalyst (IIe) and then filtered, to separate the resin. The filtrate is evaporated in vacuo and the remaining solid is treated with pentane (10 mL) and the resulting suspension is kept in an ultrasonic bath for 1 min. Solid residue is filtered, washed with methanol (5 mL) and pentane (10 mL) and dried in vacuo.

Catalyst (IIa) is obtained as a green solid (135 mg, 71% yield). $^1$H NMR (500 MHz, CDCl$_3$) δ 16.71 (s, 1H), 7.37 (t, J=7.5 Hz, 1H), 7.13 (d, J=8.3 Hz, 2H), 7.03 (s, 4H), 7.00-6.88 (m, 3H), 6.61 (d, J=8.0 Hz, 3H), 4.15 (s, 4H), 2.93 (s, 6H), 2.47 (s, 12H), 2.37 (s, 6H). $^{13}$C NMR (126 MHz, CDCl$_3$) δ 292.65, 210.50, 154.24, 143.89, 138.79, 136.22, 129.54, 129.46, 128.74, 127.69, 123.66, 122.90, 122.53, 113.86, 113.13, 51.81, 41.20, 21.24, 19.43. HRMS: m/z calcd for C$_{36}$H$_{41}$N$_3$O$_4$Cl$_2$Ru 703.16809; found: 703.1661.

Catalyst (IIb) is obtained as a green solid (142 mg, 80% yield). $^1$H NMR (300 MHz, CDCl$_3$): δ 16.71 (d, J=0.9 Hz, 1H), 7.44-7.36 (m, 1H), 7.25-7.14 (m, 5H), 7.03 (s, 4H), 7.00 (d, J=1.8 Hz, 1H), 6.94 (td, J=7.5, 0.8 Hz, 1H), 6.66 (d, J=8.3 Hz, 1H), 4.16 (s, 4H), 2.46 (s, 12H), 2.37 (s, 6H). $^{13}$C NMR (75 MHz, CDCl$_3$) δ 292.53, 210.04, 153.24, 153.04, 144.21, 138.85, 136.03, 129.52, 129.44, 126.03, 124.21, 122.82, 122.08, 51.79, 21.22, 19.44. HRMS: m/z calcd for C$_{34}$H$_{36}$N$_2$OCl$_2$Ru 660.1253; found: 660.1239.

Catalyst (IIc) is obtained as a green solid (129 mg, 69% yield). $^1$H NMR (500 MHz, CDCl$_3$) b 16.70 (s, 1H), 7.42 (t, J=7.1 Hz, 1H), 7.24-7.18 (m, 4H), 7.06-6.94 (m, 6H), 6.65 (d, J=8.1 Hz, 1H), 4.16 (s, 4H), 2.45 (s, 12H), 2.38 (s, 6H).

$^{13}$C NMR (75 MHz, CDCl$_3$) δ 292.09, 209.55, 152.61, 151.71, 144.10, 138.98, 138.83, 135.94, 131.40, 129.55, 124.60, 123.43, 122.96, 114.00, 51.80, 21.23, 19.41. HRMS: m/z calcd for C$_{34}$H$_{35}$N$_2$OCl$_3$Ru 694.0820; found: 694.0845.

Catalyst (IIe) is obtained as a green solid (139 mg, 73% yield). $^1$H NMR (500 MHz, CDCl$_3$) δ 16.59 (s, 1H), 7.49 (t, J=7.6 Hz, 2H), 7.32 (d, J=7.6 Hz, 5H), 7.22 (d, J=8.1 Hz, 2H), 6.95-6.83 (m, 2H), 6.64-6.52 (m, 3H), 4.13 (s, 4H), 3.64 (sep, J=6.2 Hz, 4H), 2.92 (s, 6H), 1.27 (d, J=6.7 Hz, 12H), 1.19 (d, J=6.4 Hz, 12H). $^{13}$C NMR (126 MHz, CDCl$_3$) δ 287.86, 213.42, 148.85, 142.88, 137.25, 129.67, 129.33, 124.67, 123.74, 123.46, 121.94, 113.73, 113.04, 54.77, 41.10, 28.70, 26.49, 24.07. HRMS: m/z calcd for C$_{42}$H$_{53}$N$_3$OCl$_2$Ru 787.2567; found: 787.2600. Elemental analysis calcd. for C$_{42}$H$_{53}$N$_3$OCl$_2$Ru (787.88): C 64.03, H 6.78, N 5.33; found C 64.56, H 6.96, N 5.12.

Catalyst (IIf) is obtained as a green solid (151 mg, 84% yield). $^1$H NMR (500 MHz, CDCl$_3$) δ 16.59 (d, J=0.5 Hz, 1H), 7.49 (t, J=7.7 Hz, 2H), 7.39-7.24 (m, 9H), 7.23-7.18 (m, 1H), 6.95 (dd, J=7.6, 1.6 Hz, 1H), 6.89 (t, J=7.4 Hz, 1H), 6.56 (d, J=8.3 Hz, 1H), 4.14 (s, 4H), 3.63 (sep, J=6.7 Hz, 4H), 1.27 (d, J=6.9 Hz, 12H), 1.17 (d, J=6.6 Hz, 12H). $^{13}$C NMR (126 MHz, CDCl$_3$) δ 287.38, 212.79, 154.03, 153.04, 148.87, 143.08, 137.11, 129.74, 129.50, 129.33, 126.46, 124.66, 123.93, 123.16, 122.19, 113.85, 54.76, 28.71, 26.51, 23.97. HRMS: m/z calcd for C$_{40}$H$_{48}$N$_2$OCl$_2$Ru 744.2185; found: 744.2178.

Catalyst (IIg) is obtained as a green solid (141 mg, 75% yield). $^1$H NMR (500 MHz, CDCl$_3$) δ 16.57 (s, 1H), 7.50 (t, J=7.7 Hz, 2H), 7.39-7.35 (m, 1H), 7.34-7.29 (m, 6H), 7.26-7.23 (m, 2H), 7.00-6.88 (m, 2H), 6.55 (d, J=8.3 Hz, 1H), 4.15 (s, 4H), 3.61 (sep, J=6.8 Hz, 4H), 1.27 (d, J=6.9 Hz, 12H), 1.18 (d, J=6.6 Hz, 12H). $^{13}$C NMR (126 MHz, CDCl$_3$) δ 286.85, 212.24, 153.61, 151.49, 148.85, 142.93, 137.00, 131.91, 129.82, 129.62, 129.37, 124.69, 124.51, 124.32, 122.34, 113.69, 54.76, 28.73, 26.49, 23.97. HRMS: m/z calcd for C$_{40}$H$_{47}$N$_2$OCl$_3$Ru 778.17584; found: 778.1784. Elemental analysis calcd. for C$_{40}$H$_{47}$N$_2$OCl$_3$Ru (778.80) C 61.63, H 6.08, N 3.60; found 61.19, H 6.16, N 3.68.

Catalyst (IIh) is obtained as a green solid (125 mg, 66% yield). $^1$H NMR (500 MHz, CDCl$_3$) δ 16.55 (s, 1H), 8.18-8.14 (m, 2H), 7.53-7.47 (m, 4H), 7.45-7.40 (m, 1H), 7.33 (d, J=7.7 Hz, 4H), 7.00-6.98 (m, 2H), 6.63 (d, J=8.3 Hz, 1H), 4.16 (s, 4H), 3.57 (sep, J=6.7 Hz, 4H), 1.27 (d, J=6.9 Hz, 12H), 1.17 (d, J=6.6 Hz, 12H). $^{13}$C NMR (126 MHz, CDCl$_3$) δ 285.70, 211.08, 157.97, 152.17, 148.89, 145.60, 143.22, 136.77, 129.97, 129.39, 126.16, 125.35, 124.71, 123.29, 122.80, 116.78, 114.27, 54.77, 28.79, 26.51, 23.89. HRMS: m/z calcd for C$_{40}$H$_{74}$N$_3$O$_3$Cl$_2$Ru 789.2032; found: 789.2029.

a) Preparation of Catalyst (IId)

A flame-dried Schlenk tube containing [RuCl$_2$(SIMes)(3-phenylindeneylidene) (py)](200 mg, 0.27 mmol; Umicore AG & Co. KG, Hanau, Germany) is evacuated and back-filled with argon three times. Tetrahydrofuran (5 mL) is added and the resulting suspension is cooled to 0° C. Then styrene-based precursor (Id) (65.7 mg, 0.27 mmol) and Amberlyst resin (275 mg, dry form, 4.70 mmol H$^+$/g) is added and the mixture is stirred at −5° C. for 30 minutes, filtered and evaporated in vacuo. The solid residue is washed with methanol (5 mL), pentane (10 mL) and dried in vacuo.

Catalyst (IId) is obtained as a green solid (141 mg, 75% yield). $^1$H NMR (500 MHz, CDCl$_3$) δ 16.69 (s, 1H), 8.12 (d, J=7.2 Hz, 2H), 7.49 (s, 1H), 7.35 (d, J=7.4 Hz, 2H), 7.04 (s, 6H), 6.79 (d, J=7.3 Hz, 1H), 4.18 (s, 4H), 2.43 (s, 12H), 2.40 (s, 6H). $^{13}$C NMR (126 MHz, CDCl$_3$) δ 291.42, 208.52, 158.38, 150.86, 145.17, 144.58, 139.16, 138.94, 129.59, 129.46, 125.78, 125.30, 123.47, 121.80, 114.94, 51.79, 21.28, 19.43.

Example 3

Catalyst Testing

The new Ru-based catalysts are exemplarily evaluated in ring-closing metathesis reactions (RCM). Furthermore, the activity is compared with a conventional catalyst known from the prior art, i.e. catalysts of formulas (a), (c) and (d).
Results of RCM Catalysts of formulas (IIa) to (IIh) are systematically tested for a number of ring closing metathesis reactions leading to N-heterocycles. A comparison with prior art catalyst (a) is made.

The ring-closing reactions are carried out in toluene at 50° C. with a reaction time of 15 min. The substrate is present in an amount of 0.5 mol/L. Reactions are carried out in sealed 10 mL Schlenk tubes under an atmosphere of argon. In a 10 mL Schlenk tube, substrate is dissolved in dry toluene under an atmosphere of argon. This solution is heated to 50° C. and catalyst (0.0025 to 0.02 mol-%) (25 to 200 ppm) from a stock solution (0.75 mmol/L) in toluene is added. The latter is prepared by adding $4.0 \cdot 10^{-6}$ mol of catalyst (IIa) to (IIh) into a 10 mL Schlenk tube, evacuating the tube, filing the tube with argon and subsequent addition of 5.34 mL of dried toluene under a stream of argon. The Schlenk tube is kept in an ultrasonic bath for 1 min for complete dissolution of the inventive catalyst.

The substrate concentration is defined as $c(S)=n(S)/(V(S)+V(toluene)+V(stock\ solution))$. For the determination of substrate conversion, samples (10 μL, substrate conc. 0.5 M) are taken after the specified times under a stream of argon and injected into GC vials containing 250 μL of a 25% (v/v) ethyl vinyl ether solution in toluene. The conversions are determined by GC. The degree of conversions is the average conversion of two runs. The results are presented in Table 1.

The catalysts according to the present invention allow for excellent substrate conversions of ≥60% within less than 15 minutes of reaction time at a low catalyst loading of between and at low to moderate temperatures. For the majority of RCM substrates a conversion of even about 90% or higher within 15 minutes of reaction time is measured.

In this context, the new Ru-based catalysts of the present invention seem to be especially efficient in RCM reactions leading to di- or tri-substituted cyclic olefins (ref to Table 1, entry 6 and Table 2).

TABLE 1

Conversion (in %) in RCM reactions of various substrates for catalysts of the invention (IIa to IIh) and prior art catalyst (a) at different catalyst loadings

| Entry | Substrate | Catalyst loading [ppm] | Conversion (%) | | | | | | | |
|---|---|---|---|---|---|---|---|---|---|---|
| | | | (a) | IIa | IIb | IIc | IId | IIe | IIf | IIg | IIh |
| 1 | Tos-N(allyl)(allyl) | 25 | 70 | 83 | 90 | 73 | 83 | 99 | — | 81 | 99 |
| 2 | Tos-N(allyl)(homoallyl) | 15 | — | — | 74 | 64 | — | 91 | 96 | 78 | 92 |
| 3 | Boc-N(allyl)(homoallyl) | 50 | 60 | 71 | 60 | — | 54 | 89 | 91 | — | 83 |
| 4 | Boc-N(allyl)(allyl) | 50 | — | — | 91 | — | 80 | — | 98 | — | — |
| 5 | Tos-N(homoallyl)(homoallyl) | 200 | — | 92 | 92 | — | 77 | 99 | 99 | — | 98 |
| 6 | Tos-N(allyl)(methallyl) | 50 | 39 | — | 61 | — | — | 90 | 72 | — | 84 |

Reaction conditions: Toluene solvent, 0.5M substrate, T = 50° C., reaction time 15 minutes, conversions detected by GC, average of two runs.

Apart from the low catalyst loading, the short reaction time required for such reactions is most notable—all of the reactions studied are almost completed within less than 15 min.

TON and TOF are calculated for substrate of entry no. 4 and catalyst (IIf). Accordingly, by using catalyst (IIf) a TON of $6.4 \times 10^4$ and a TOF of $2.56 \times 10^5$ h$^{-1}$ is observed. This is a significant improvement with respect to the prior art.

Catalyst of formula (IIb) is tested under the above mentioned conditions for a ring closing metathesis reaction with a more complicated and critical substituted olefinic substrate in comparison with N-chelated Grubbs-Hoveyda-type catalysts of formulas (c) and (d) known from the prior art.

TABLE 2

Conversion (in %) in RCM reactions for catalyst (IIb) of the invention and prior art catalysts (c) and (d)

| Substrate | Catalyst loading [ppm] | Conversion (%) | | |
|---|---|---|---|---|
| | | (c) | (d) | IIb |
| EtO₂C CO₂Et | 50 | 58 | 54 | 78 |

Reaction conditions: Toluene solvent, 0.5M substrate, T = 50° C., reaction time 15 minutes, conversions detected by GC, average of two runs.

Comparative Tests with Prior Art Catalysts

In the RCM of N,N-diallyltosylamide at 0° C. catalysts of formula (IIb) and (IIf) are significantly faster than the prior art catalyst (a). At low temperatures fast initiation translates into excellent catalytic activities compared to catalyst (a) known from the art, which initiate considerably more slowly. FIG. 1 shows the results of the RCM reaction. After 120 min a complete conversion is almost obtained for catalysts (IIb) and (IIf), while it takes much longer for the less rapidly initiating catalyst (a). The faster activation of catalysts (IIb) and (IIf) is evident from the faster initial transformation of the substrate to the respective RCM product.

Figure 2:
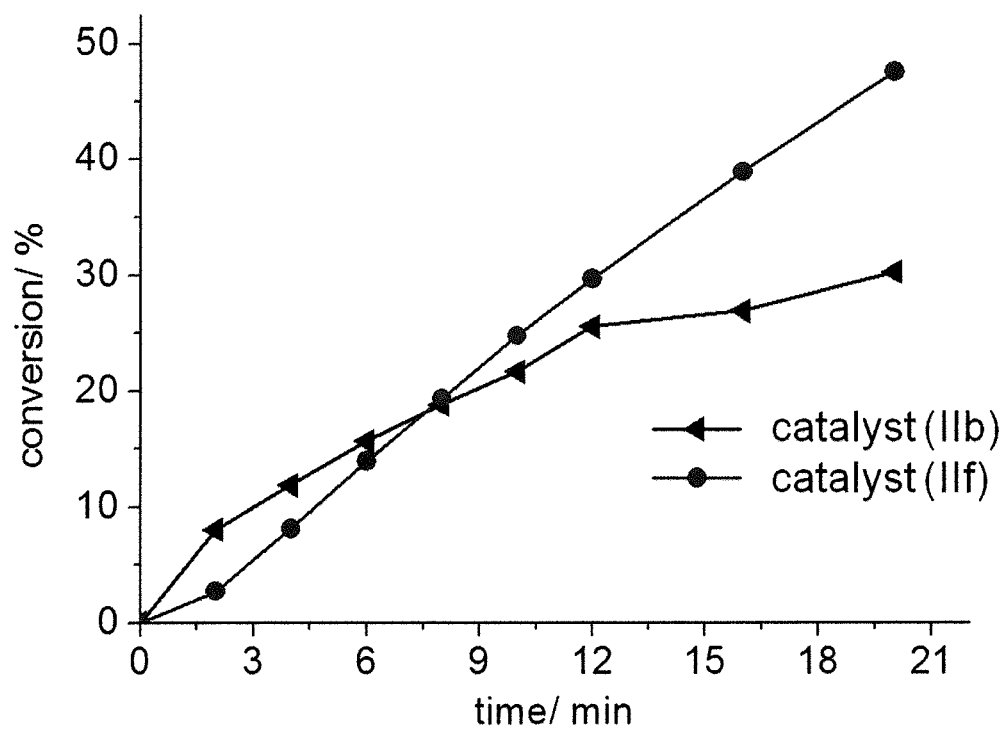
FIG. 2 shows the conversion (in %) of N,N-diallyltosylamide (0.1 mol/L) during RCM reaction over a reaction period of 20 minutes at 0° C. in toluene using 0.025 mol-% (250 ppm) of catalysts of formulas (IIb) and (IIf).
Figure 3:
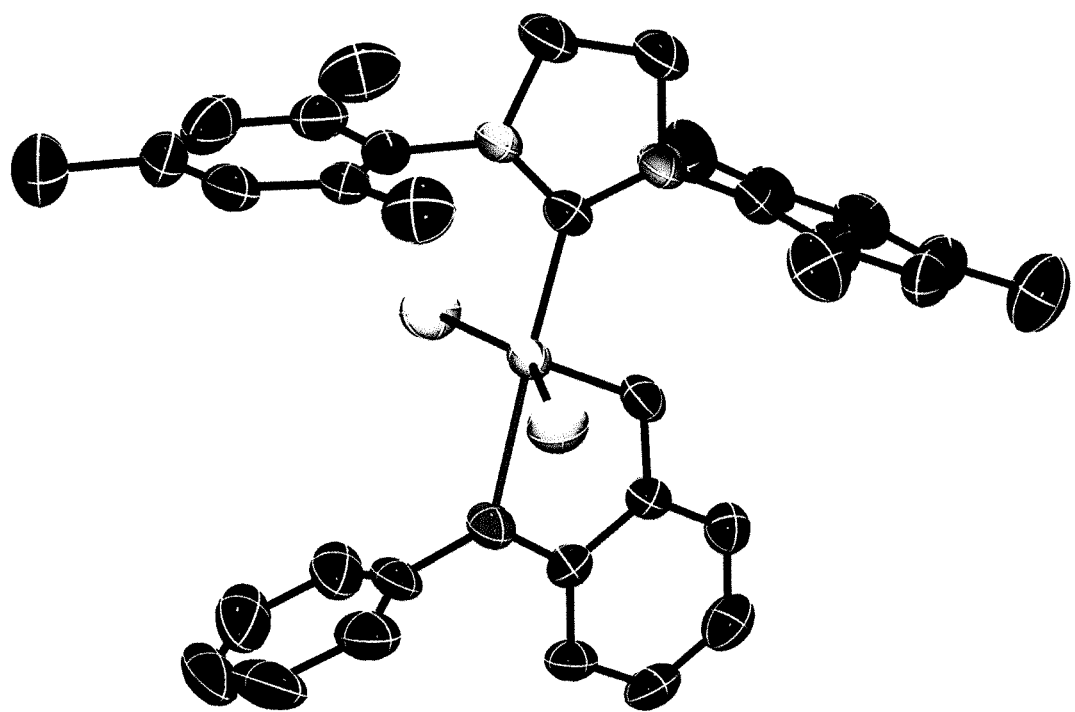
FIG. 3 shows an ORTEP plot of the crystal structure of catalyst (IIb). Important bond lengths (pm) and angles (°) are (two independent molecules of catalyst (IIb) are observed in solid state, which differ with respect to the orientation of the phenyl group relative to the rest of the molecule, the first number corresponds to molecule 1 followed by the respective data for molecule 2): Ru—O 226.6(4), 230.5(3); Ru—C (NHC) 198.4(5), 197.0(6); Ru=CHR 182.1(5), 180.9(5), Ru—Cl 230.7(2), 232.3(2), 232.1(2), 234.0(2); Cl—Ru—Cl 153.71(6), 158.31(6). The significant variability of the Ru—O distances in the two observed molecules of catalyst (IIb) indicates that there is a shallow energy potential curve for the Ru—O bond and, thus, an increased sensibility of the bond with regard to minor disturbances.
Figure 4:
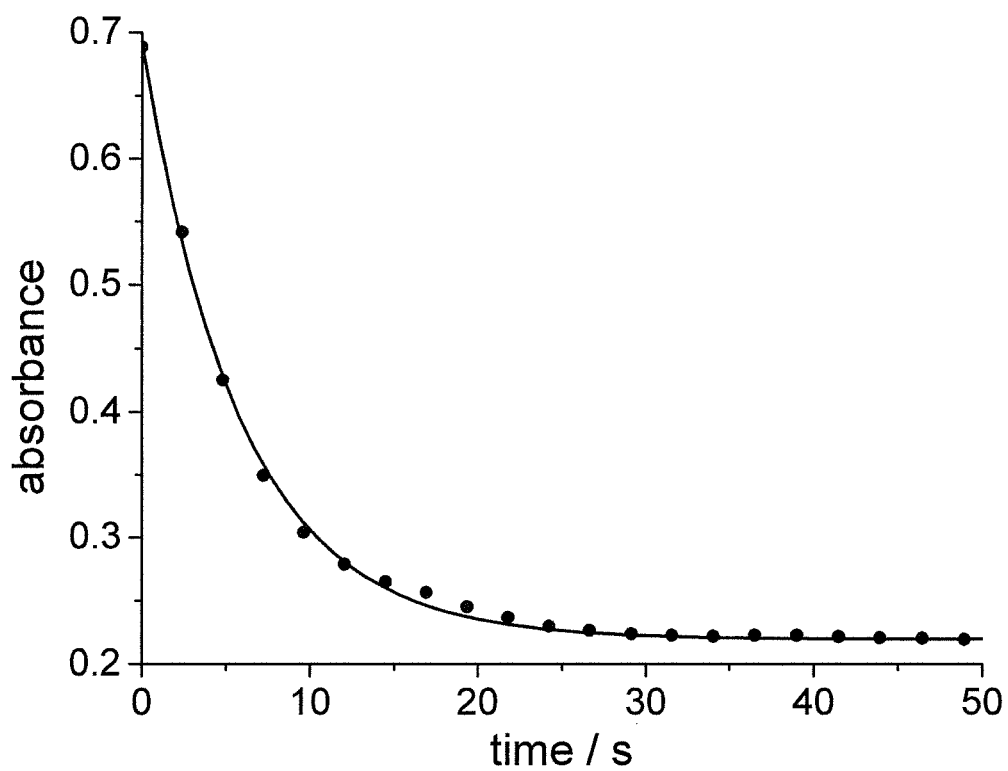
FIG. 4 shows the absorbance-time curve of catalyst (IId) (1×10$^{-4}$ mol/L) during reaction with butyl vinyl ether (0.01 M) in toluene at 30° C. The data are fitted using (y=A1·exp(−x/t$_1$)+y0) and (k$_{obs}$=1/t$_1$). The absorbance of catalyst (IId) probably resulting from the ligand-metal-charge transfer (LMCT band) is measured at 370 nm. A fast decrease of the absorbance of catalyst (IId) was observed. The dissociation reaction required less than 20 seconds, even at a very low concentration of butyl vinyl ether (0.01 mol/L) and at a temperature, which was slightly above ambient temperature (30° C.). From this it is evident that the Ru—O bond is broken rapidly in the presence of the olefin.

The fast initiation and substrate conversion is also evident from FIG. 2, which gives a detailed view on the conversion (in %) of N,N-diallyltosylamide within the first 20 minutes for catalysts (IIb) and (IIf). Accordingly, a conversion of more than 20% is obtained even within 9 minutes at 0° C. Figure also shows that catalyst (IIb) initiates faster than catalyst (IIf).

The increased catalytic activity of the catalysts according to the present invention compared with prior art catalyst (a) is also confirmed in Table 1. According to Table 1, the catalysts of the present invention show a considerably higher activity in RCM reactions with different substrates.

Furthermore, a strong influence of temperature on the catalyst performance is noted. In order to obtain about 85% yield in the RCM of N,N-diallyltosylamide at 0° C., about 250 ppm of the catalyst of formula (IIf) are required at a reaction time of about 180 min. At 50° C. a yield of 96% is obtained within 15 min using only 15 ppm of the catalyst of formula (IIf) (ref to Table 1).

Still further, from Table 2 it is evident that catalyst (IIb) enables superior conversion rates of important and more critical substrates such as diethylallyl-(2-methylallyl)malonate compared with the N-chelated catalysts known from the prior art. Considering the more complicated synthesis of N-chelated catalysts as well as the stability of N-chelated Grubbs-Hoveyda-type catalysts, which is usually limited, the Ru-based catalysts according to the present invention provide exceptional advantages in view of the catalysts already known.

The invention claimed is:

1. A compound of formula (I) for the preparation of ruthenium-based catalysts

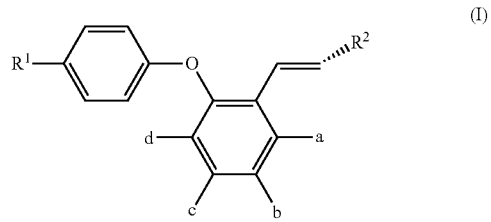

wherein
a, b, c and d are, independently from each other, selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, optionally substituted $C_6$-$C_{14}$-aryl, optionally substituted $C_6$-$C_{14}$-aryloxy, optionally substituted $C_6$-$C_{14}$-heteroaryl;

$R^1$ is hydrogen, straight chain or branched $C_1$-$C_{10}$-alkylthio, $C_1$-$C_{10}$-silyloxy, $C_1$-$C_{10}$-alkylamino, $C_1$-$C_{10}$-dialkylamino, or electron-withdrawing groups (EWG) selected from the group consisting of trifluormethyl (—$CF_3$), nitro (—$NO_2$), formyl (—CHO), $C_1$-$C_{10}$-carboxyl, $C_1$-$C_{10}$-alkylamido, $C_1$-$C_{10}$-aminocarbonyl, nitrile (—CN) or $C_1$-$C_{10}$-sulfonamide;

$R^2$ is hydrogen, straight chain or branched $C_1$-$C_{10}$-alkyl groups.

2. The compound according to claim 1, wherein
a, b, c and d each are hydrogen;
$R^1$ is dimethylamino ($NMe_2$-), nitro ($NO_2$—); and
$R^2$ is hydrogen, methyl, ethyl, n-propyl, iso-propyl, n-butyl or iso-butyl.

3. The compound according to claim 2, having the formula (Ia)

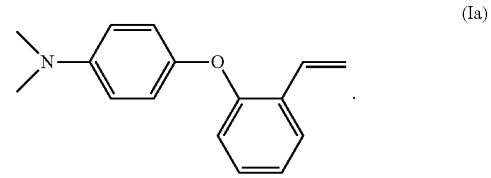 [SMILES: C=Cc1ccccc1Oc1ccc(N(C)C)cc1]

4. A method for preparing the catalyst according to claim 1, comprising reacting a compound of formula (I)

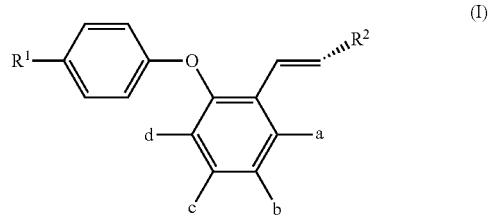

wherein
a, b, c and d are, independently from each other, selected from hydrogen, straight chain or branched alkyl groups including $C_1$-$C_{10}$-alkyl, $C_1$-$C_{10}$-alkoxy, $C_1$-$C_{10}$-alkylthio, $C_1$-$C_{10}$-silyloxy, $C_1$-$C_{10}$-alkylamino, optionally substituted $C_6$-$C_{14}$-aryl, optionally substituted $C_6$-$C_{14}$-aryloxy, optionally substituted $C_6$-$C_{14}$-heteroaryl;

$R^1$ is straight chain or branched $C_1$-$C_{10}$-alkylthio, $C_1$-$C_{10}$-silyloxy, $C_1$-$C_{10}$-alkylamino, $C_1$-$C_{10}$-dialkylamino, or electron-withdrawing groups (EWG) selected from the group consisting of trifluormethyl (—$CF_3$), nitro (—$NO_2$), formyl (—CHO), $C_1$-$C_{10}$-carboxyl, $C_1$-$C_{10}$-alkylamido, $C_1$-$C_{10}$-aminocarbonyl, nitrile (—CN) or $C_1$-$C_{10}$-sulfonamide:

$R^2$ is hydrogen, straight chain or branched $C_1$-$C_{10}$-alkyl groups with a Ru-starting compound having the formula (V):

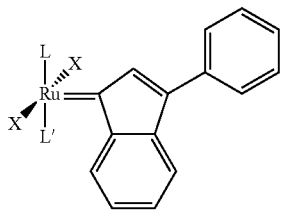

(V)

in a cross metathesis reaction,
wherein
L is a phosphine ligand selected from the group of tri-iso-propyl-phosphine, tricyclohexylphosphine ($PCy_3$), tricyclopentylphosphine, cyclohexylphobane, 2,2,4-trimethylpentylphobane or isobutyl-phobane or a NHC ligand selected from the group of 1,3-bis-(2,4,6-trimethylphenyl)-imidazolidine-2-ylidene ("SIMes"), 1,3-bis-(2,6-di-isopropylphenyl)-imidazolidine-2-ylidene ("SIPr") or 1,3-bis-(2, 6-diisopropylphenyl)-imidazoline-2-ylidene ("IPr") and L' is a leaving ligand from the group of tri-iso-propylphosphine, tricyclohexylphosphine ($PCy_3$), tricyclopentylphosphine, cyclo-hexylphobane, 2,2,4-trimethylpentyl-phobane, isobutylphobane or substituted or unsubstituted pyridine ligands;

X is an anionic ligand selected from the group of halogen anions ($Cl^-$, $Br^-$, $I^-$).

5. The method for preparing the catalysts according to claim 4, wherein
L is a NHC ligand selected from the group of 1,3-bis-(2, 4,6-trimethylphenyl)imidazolidine-2-ylidene ("SIMes"), 1,3-bis-(2,6-di-isopropylphenyl)-imidazolidine-2-ylidene ("SIPr") or 1,3-bis-(2,6-di-isopropylphenyl)-imidazoline-2-ylidene ("IPr"),
L' is pyridine,
X is $Cl^-$.

\* \* \* \* \*